United States Patent [19]
Jaen et al.

[11] Patent Number: 5,340,808
[45] Date of Patent: Aug. 23, 1994

[54] FUSED PYRIDAZINOQUINAZOLONE DERIVATIVES AS NEUROTROPHIC AGENTS

[75] Inventors: Juan C. Jaen, Plymouth; Bradley W. Caprathe, Redford, both of Mich.

[73] Assignee: Warner Lambert Company, Ann Arbor, Mich.

[21] Appl. No.: 976,147

[22] Filed: Nov. 13, 1992

[51] Int. Cl.$^5$ .................. A61K 31/505; A61K 31/55; C07D 487/04; C07D 487/14
[52] U.S. Cl. ..................................... 514/248; 514/214; 544/224; 544/233; 544/234; 544/239; 540/578; 560/22
[58] Field of Search ................. 544/233, 234; 514/248

[56] References Cited

U.S. PATENT DOCUMENTS 4,250,177  2/1981  Schwender et al. ................ 424/250

OTHER PUBLICATIONS

Schwender et al., *J. Med. Chem.*, 1980, 23, pp. 964–966.

*Primary Examiner*—Emily Bernhardt
*Attorney, Agent, or Firm*—Merchant, Gould, Smith, Edell, Welter & Schmidt

[57] ABSTRACT

Fused pyridazinoquinazoline compounds, salts thereof, methods of production, intermediates in their production, pharmaceutical compositions containing said compounds and methods for treating neurodegenerative disorders using said compositions are disclosed.

11 Claims, No Drawings

FUSED PYRIDAZINOQUINAZOLONE DERIVATIVES AS NEUROTROPHIC AGENTS

FIELD OF THE INVENTION

The present invention relates to novel pyridazinoquinazolone compounds and pharmaceutical compositions containing pyridazinoquinazolone compounds that are useful pharmacological agents in the treatment of a variety of neurodegenerative disorders, methods for production of the compounds, and methods for treating neurodegenerative disorders.

BACKGROUND ART

Nerve growth factor (NGF) was first described by Levi-Montalcini (J. Exp. Zool. 116:321-362, 1951) as an activity secreted by a mouse sarcoma tumor implanted into a chick embryo. Both sensory ganglion and sympathetic ganglion neurons grew neurites into the sarcoma, which also supported the growth of peripheral neurons in culture. The factor, purified to homogeneity from mouse submandibular glands in 1956 by Levi-Montalcini and Cohen (Proc. Natl. Acad. Sci. USA 42:571, 1956) consists of a complex (referred to as 7S NGF, from its sedimentation coefficient) comprised of three different subunits. NGF's neurotrophic activity resides entirely within the $\beta$-subunit (hereinafter referred to as NGF), a dimer consisting of two equivalent monomers of approximately 13,000 dalton molecular weight.

A role for NGF as a neurotrophic factor in the peripheral nervous system (PNS) was rapidly established through both in vitro and in vivo experiments (Levi-Montalcini and Angeletti, Physiol. Rev. 48:534-569, 1968; Johnson, et al., Science 210:916-918, 1980). These studies demonstrated that sympathetic neurons of the PNS have an absolute requirement for NGF for survival throughout life, while many sensory neurons require NGF during certain periods of development. As an extrapolation of these early findings, NGF and related neurotrophic factors have been shown recently to be useful in the treatment of sensory and autonomic neuropathies (Kaplan, et al., Science 252:554-558, 1991). More specifically, NGF prevents the development of small-fiber sensory neuropathies that result from the use of taxol, a chemotherapeutic agent (Apfel, et al., Ann. Neurol. 29:87-90, 1991). NGF is also efficacious against the development of large-fiber sensory neuropathies resulting from the anticancer drug cisplatin, and in an animal model of diabetes-induced neuropathy (Apfel, et al., Ann. Neurol. 31:76-80, 1992).

NGF is synthesized in the periphery by the non-neuronal target tissues innervated by the NGF-dependent neurons. Upon binding of NGF to its receptor, the NGF receptor complex is internalized by the neuron and retrogradely transported back to the neuron cell body. NGF's intracellular mechanism of action is not yet fully understood.

It was not until 1983 that NGF was detected in the central nervous system (CNS) (Ayer-LeLievre, et al., Medical Biology 61:296-304, 1983). This discovery was preceded by the demonstration that the cholinergic neurons of the basal forebrain are responsive to NGF (Schwab, et al., Brain Res. 168:473-483, 1979). These neurons possess NGF receptors which are undistinguishable from the NGF receptors in the periphery. As in the PNS, NGF is synthesized by the target regions of the sensitive neurons, the hippocampus and the neocortex. NGF secreted by these target regions binds to its receptor on NGF-dependent neurons, and is required for the development and survival of these neurons. The NGF receptor, generally known as p75 because it has a molecular weight of about 75,000 daltons, has recently been cloned (Johnson, et am., Cell. 47:544-554, 1986).

In animal models, lesions of the septo-hippocampal neuronal pathway, which connects the neurons of the basal forebrain to the hippocampus, results in the degeneration of the neurons in the medial septal nucleus, due to the lack of trophic support that is normally provided by hippocampal NGF. This neuronal degeneration can be prevented by administration of NGF into the cerebrospinal fluid (CSF) of the animals via a miniosmotic pump [Gage, et al., J. Comp. Neurol. 269:147-155, 1988; Hagg, et al., Exp. Neurol. 101:303-312, 1988; Kromer, et al., Science 235:214-216, 1987]. NGF also enhances the ability of brain cholinergic neurons to survive a chemical insult. In animals with atrophied or lesioned basal forebrain cholinergic neurons, NGF has been shown to reverse the associated behavioral impairment (Fisher, et al., J. Neurosci, 11:1889-1906, 1991; Tuszynski, et al., Ann. Neurol. 30:625-636, 1991).

Even though there is no direct evidence for a reduced level of NGF in neurodegenerative disorders such as Alzheimer's disease (AD), the sensitivity of brain cholinergic neurons to NGF treatment is specially interesting, since these neurons are consistently depleted in AD. In fact, recent clinical findings in humans support the interpretation that treatment with NGF is useful in the treatment of AD (Olson, et al., J. Neural Transm. (D-P Sect) 4:79, 1992).

NGF is a member of a family of related neurotrophic peptides, the neurotrophins, all with a high degree of similarity in terms of their molecular weight and amino acid sequence. Other representative members of the neurotrophins include brain derived neurotrophic factor (BDNF) and neurotrophin-3 (NT-3). While these peptides are selectively expressed in discrete areas of the brain of mammals, they all seem to bind to the same p75 receptor as NGF (Squinto, et al., Cell 65:885-893, 1991), and they seem to possess neurotrophic activity at well-defined populations of neurons. For instance, BDNF exerts neurotrophic effects on substantia nigra dopaminergic neurons (Knuesel, et al., Proc. Acad. Sci. USA, 1991, (88), 961-965). Since degeneration of these neurons is directly responsible for Parkinson's disease (PD), it is conceivable that BDNF will be useful in the treatment of this devastating disease.

AD, PD and drug-induced peripheral neuropathies are but a few of the many neurodegenerative conditions that might be amenable to neurotrophic treatment. However, as mentioned above, NGF and related neurotrophins are large peptides (around 120 amino acids), which large size makes them unlikely therapeutic candidates. In addition to the lack of a ready source of endogenous peptide(s), these compounds possess very poor pharmacokinetic parameters (e.g. poor oral absorption, short in-vivo half-life) and administration to the target organs also represents a major problem. One solution requires the use of cerebral implants of genetically engineered cells (Rosenberg, et al., Science 242:1575-1578, 1988) or intracerebral pumping devices for continuous infusion of the peptide (Powell, et al., Brain Res. 515:309-311, 1990). For these reasons, it would be extremely useful to identify novel compounds with physicochemical properties different from the neurotrophins but still able to interact with the neurotrophins' p75 receptor. The ideal compounds would be non-peptides, since this would enhance in vivo half-life. The non-peptides would be much smaller in molecular size than the endogenous peptides, and this would be expected to enhance oral absorption and CNS penetration. The present invention describes the identification of such a group of compounds that bind to the p75 receptor, which binding may stimulate neuronal regeneration and thus be useful in the neurotrophic treatment of a variety of neurodegenerative disorders.

SUMMARY AND DETAILED DESCRIPTION

In one aspect, the invention concerns pyridazinoquinazole compounds that have use in their capacity to bind the p75 receptor of the neurotrophins and thus are useful in dosage form in the treatment of CNS neuro-degenerative disorders such as Alzheimer's disease, Parkinson's disease, Huntington's chorea, and the like, and PNS neurogenerative disorders such as drug-induced peripheral neuropathies and the like.

More particularly, the invention relates to pyridazinoquinazolone compounds of the formula I

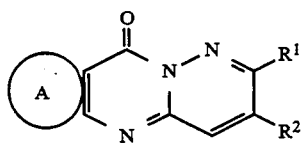

and salts thereof, wherein

is a moiety selected from

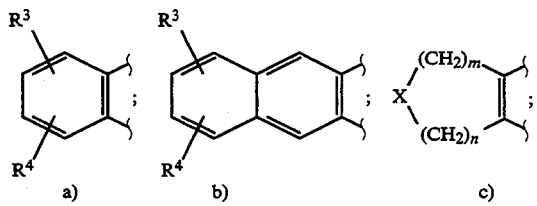

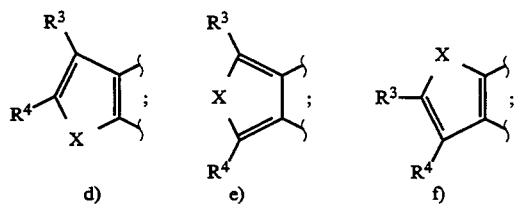

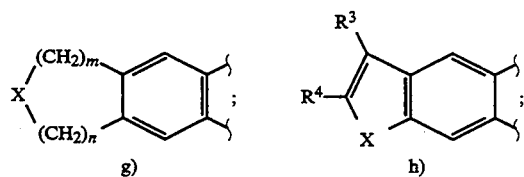

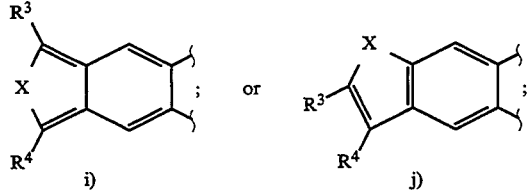

one of $R^1$ and $R^2$ is an acid group selected from —COOH, —SO$_3$H,

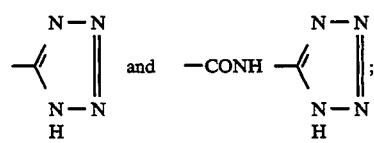

and the other of $R^1$ and $R^2$ is H or alkyl:

$R^3$ and $R^4$ can independently be H, alkyl, aryl, —COOH, —CONH$_2$, —CO—NH—aryl, CO—NH-arylalkyl, —CO—NH-alkyl, —CO—NH-arylalkyl, CO—NH-cycloalkyl, —CO—NH-alkylaryl, —NH$_2$, —NHCO-alkyl, —NHCO-alkylaryl, or —NHCO-N(R$^5$)R$^6$ wherein $R^5$ and $R^6$ can independently be H, alkyl or aryl, m and n can independently be 0, 1 or 2; and X is O, S or NH;

provided that, for a compound I having moiety a):

1) wherein $R^1$ is COOH and $R^2$ is H, $R^3$ and $R^4$ represent a combination other than H and H, H and Cl, H and OMe, H and Me and provided further that, for a compound I having moiety b): wherein $R^1$ is COOH and $R^2$ is H, $R^3$ and $R^4$ represent a combination other than H and H.

Preferred compounds are those wherein $R^1$ is selected from the group consisting of —COOH,

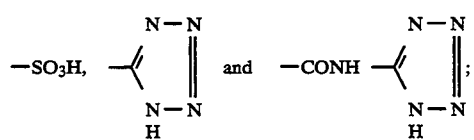

$R^2$ is H or alkyl; and

is a moiety selected from

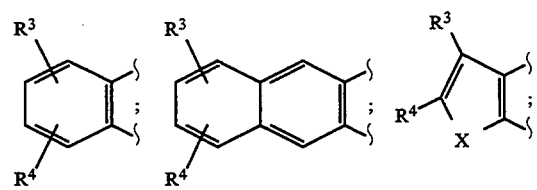

-continued

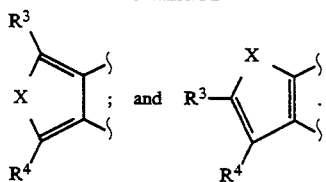

Especially preferred compounds are those wherein $R^1$ is selected from the group consisting of

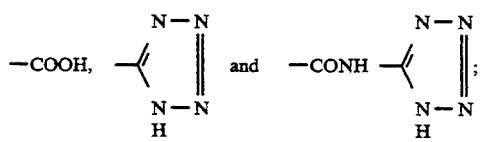

$R^2$ is H or methyl; and

is a moiety selected from

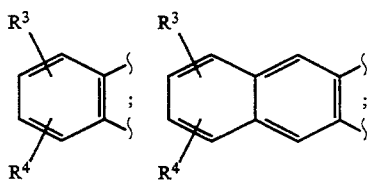

where one of $R^3$ and $R^4$ is H and the other is selected from H, —$NH_2$, —NHCO-aryl, and —COOH.

The term "alkyl" is intended to mean a hydrocarbon moiety which may be straight, branched or cyclic in configuration having from one to six carbon atoms.

The term "salts" is intended to mean salts formed by the addition of a base with those compounds of the invention capable of forming a salt, such as those compounds containing a carboxy or tetrazole group. Typical salts would be the sodium, potassium, calcium, ammonium, organic amino, or magnesium salt, or a similar salt. The preferred salts are relatively non-toxic, thus pharmaceutically acceptable salts, preferably the sodium salt. Some of the compounds of this invention may form acid addition salts with strong acids, such as hydrochloric acid.

The following compounds which are useful in dosage form according to the invention are known in the literature for their effects as anti-allergic agents. The compounds are prepared by the method of Schwender, C. F.; Sunday, B. R. and Kerbleski, J. J. Antiallergy Activity of 10-Oxo-10H-pyridazino[6,1-b]-quinazoline-2-carboxylic Acids. *J. Med. Chem.* 1980, 23, 964–966:

10-Oxo-10H-pyridazino[6,1-b]quinazoline-2-carboxylic acid
 8-Chloro-10-oxo-10H-pyridazino[6,1-b]quinazoline-2-carboxylic acid
 8-Methoxy-10-oxo-10H-pyridazino[6,1-b]quinazoline-2-carboxylic acid
 8-Methyl-10-oxo-10H-pyridazino[6,1-b]quinazoline-2-carboxylic acid
 7-Methyl-10-oxo-10H-pyridazino[6,1-b]quinazoline-2-carboxylic acid
 12-Oxo-12H-benzo[g]pyridazino[3,2-b]quinazoline-2-carboxylic acid The compounds of the invention may be prepared by methods that are illustrated in the following Schemes I, II, III, and IV.

Scheme I

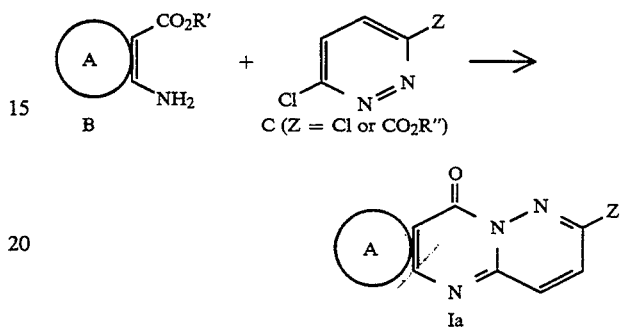

Scheme II

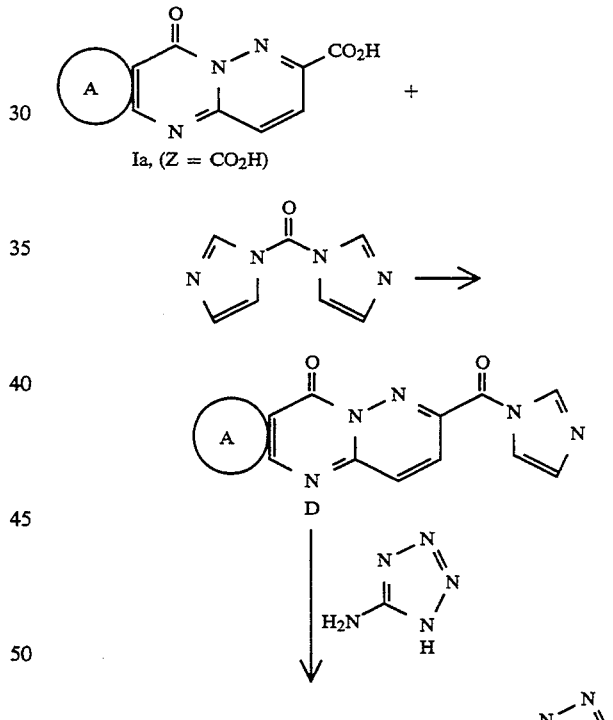

Scheme III

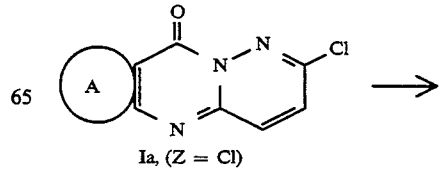

-continued

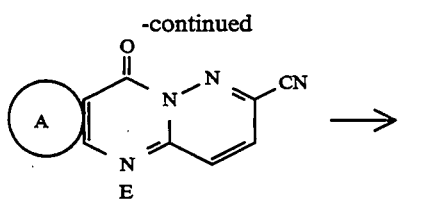

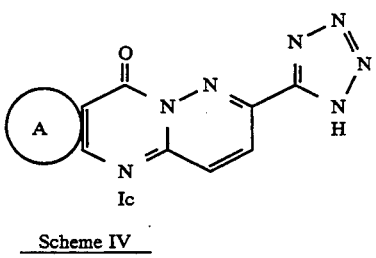

Scheme IV

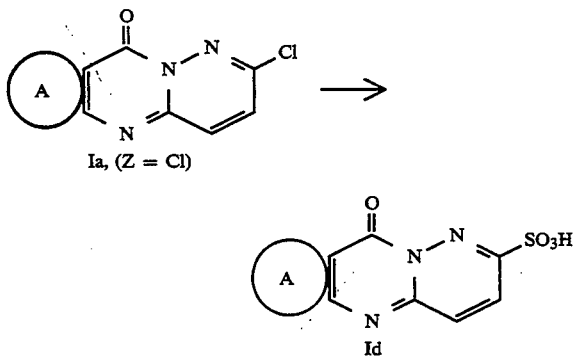

In Scheme I, condensation of the appropriately substituted aromatic ortho aminoacid (B,R'=H or alkyl) with either 3,6-dichloropyridazine (C, Z=Cl) or 6-chloropyridazine-carboxylate (C, Z=CO₂H or CO₂R') gives the pyridazoloquinazolones (Ia).

In Scheme II, the tetrazol-5-ylamides (Ib) are made from the acids (Ia,Z=COOH) and 1H-tetrazol-5-amine, using 1,1'-carbonyldiimidazole as a coupling agent.

In Scheme III, the tetrazoles (Ic) are prepared via the sequence of the chloropyridazoloquinazolone (Ia, Z=Cl) to the nitrile (E,Z=CN) and then to the tetrazoles by methods known in the art.

In Scheme IV, the chloro compounds (Ia,Z=Cl) are reacted with n-butyllithium or t-butyllithium to exchange the halogen for metal followed by reaction of the organometallic intermediate with ClS(O₂)X (where X=Cl or O-alkyl) and then acidic hydrolysis to provide the desired sulfonic acid analogue (Id).

Certain of the compounds of this invention are capable of existing in the form of hydrates or solvates. For the purposes of this invention, these other forms of the compounds are considered equivalent to the non-hydrated or non-solvated compounds and are intended to be encompassed within the scope of the invention.

As indicated, compounds of this invention are useful pharmaceutical agents. More specifically, the compounds are useful as active agents in the treatment of neurodegenerative disorders of the CNS such as Alzheimer's disease, Parkinson's disease, Huntington's chorea, and like disorders, and neurodegenerative disorders of the PNS, such as drug-induced peripheral neuropathies and the like.

The compounds may be administered orally or parenterally or by direct injection into the target organ. The usual human dosage ranges for a 80 kg subject from about 1 mg to about 1 g per day (0.01 mg to 10 mg per kg of weight per day), preferably 10 mg to 100 mg per day (0.1 mg to 1.0 mg per kg of weight per day), optionally in divided portions.

The above employed pharmaceutical compositions are produced by formulating a compound of the foregoing formula (active ingredient) in dosage unit form with a pharmaceutical carrier. Some examples of dosage unit forms are tablets, capsules, lozenges, and pills; as well as powders and aqueous and non-aqueous oral solutions and suspensions and parenteral solutions, packaged in containers containing either one or some larger number of dosage units and capable of being subdivided into individual doses by such means as measurement into a teaspoon or other standard container. Some examples of suitable pharmaceutical carrier, including pharmaceutical diluents, are gelatin capsules; sugars such as lactose and sucrose; starches such as corn starch and potato starch; cellulose derivatives such as sodium carboxymethyl cellulose, ethyl cellulose, methyl cellulose, and cellulose acetate phthalate; gelatin; talc, stearic acid; magnesium stearate; vegetable oils such as peanut oil, cotton-seed oil, sesame oil, olive oil, corn oil, and oil of theobroma; propylene glycol; glycol; glycerine, sorbitol; polyethylene glycol; water; agar; alginic acid; isotonic saline, and phosphate buffer solutions; as well as other compatible substances normally used in pharmaceutical formulations. The compositions of the invention can also contain other components such as coloring agents, flavoring agents, and/or preservatives. These materials, if present, are usually used in relatively small amounts. The compositions can, if desired, also contain other therapeutic agents.

The percentage of the active ingredient in the foregoing compositions can be varied within wide limits but for practical purposes it is preferably present in a concentration of at least 10% in a solid composition and at least 2% in a primarily liquid composition. The most satisfactory compositions are those in which a much higher proportion of the active ingredient is present. The compositions of the invention preferably contain from 2 mg. to 1.0 g of the active ingredient per dosage unit so that the entire amount to be administered during a day can be made up from a reasonable number of dosage units.

The p75 receptor binding activity of the compounds of this invention has been determined using an assay described as follows.

DESCRIPTION OF THE ASSAY USED TO DETERMINE BINDING OF COMPOUNDS TO THE NGF p75 RECEPTOR

Binding assays of novel compounds to the NGF p75 receptor are performed using a truncated form (residues 1-222, molecular weight=56 KDa) of the p75 receptor, originally obtained from Chiron Corporation, Emeryville, Calif., but also commercially available from Austral Biologicals, Inc. (San Diego, Calif.), on plastic 96 well microtiter plates (Immulon II Dynatech). The wells are coated with 50 μl/well of 20 μg/ml streptavidin in a diphosphate buffer solution (DPBS). The plates are then incubated at room temperature for 6 hours. The excess streptavidin is then poured out, the wells are washed with a 0.1% solution of bovine serum albumin (BSA) in DPBS. To each well is then added 50 μg/ml of a DPBS solution containing the truncated p75 receptor, which has previously been reacted with biotin by standard procedures. The plates are then incubated at room temperature for 2 hours, and washed with 0.2% BSA/DPBS. To each well is added 98 μl of 2 nM $^{125}$I-NGF, followed by 2 μl/well of a concentration of test compound that is 50 times greater than the desired final test concentration. The plates are incubated for 2 hours at room temperature. The assay is read as the IC$_{50}$, the concentration of compound that blocks 50% of the binding of $^{125}$I-NGF to the p75 receptor.

The activity of preferred compounds is given in the accompanying table.

was saturated with hydrogen chloride gas for 15 min. The mixture was refluxed for 12 h, cooled concentrated, dissolved into chloroform and washed with saturated sodium bicarbonate solution. The chloroform extract was dried (MgSO$_4$), filtered and concentrated to give dimethyl-4-aminoisophthalate as an off-white solid, mp 127°–130° C.

Step C. A mixture of ethyl 6-chloro-3-pyridazinecarboxylate (0.29 g, 1.55 mmol, Example 1, Step A) and dimethyl 4-aminoisophthalate (0.36 g, 1.72 mmol, Ex-

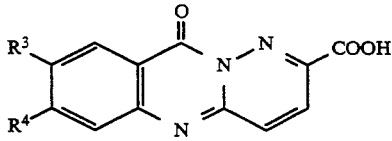

| R$_3$ | R$_4$ | Inhibition of $^{125}$I-NGF Binding to p 75 (IC$_{50}$, nM) | Names |
| --- | --- | --- | --- |
| H | H | 39% inh at 10,000 nM | 10-Oxo-10H-pyridazino[6,1-b]quinazoline-2-carboxylic acid |
| Cl | H | 4,000 | 8-Chloro-10-oxo-10H-pyridazino[6,1-b]quinazoline-2-carboxylic acid |
| OMe | H | 1,500 | 8-Methoxy-10-oxo-10H-pyridazino[6,1-b]quinazoline-2-carboxylic acid |
| Me | H | 1,800 | 8-Methyl-10-oxo-10H-pyridazino[6,1-b]quinazoline-2-carboxylic acid |
| COOH | H | 2,195 | 10-Oxo-10H-pyridazino[6,1-b]quinazoline-2,8-dicarboxylic acid |
| NHCOC$_6$H$_5$ | H | 67 | 8-(Benzoylamino)-10-oxo-10H-pyridazino[6,1-b]-quinazoline-2-carboxylic acid |
| NHCO-4-MeC$_6$H$_4$ | H | 238 | 8-[(4-Methylbenzoyl)amino]-10-oxo-10H-pyridazino [6,1-b] quinazoline-2-carboxylic acid |
| H | Me | 4,900 | 7-Methyl-10-oxo-10H-pyridazino[6,1-b]quinazoline-2-carboxylic acid |
| H | COOH | 46% inh at 10,000 nM | 10-Oxo-10H-pyridazino[6,1-b]quinazoline-2,7-dicarboxylic acid |
| H | NHCOMe | 42% inh at 10,000 nM | 7-Acetylamino-10-oxo-10H-pyridazino[6,1-b]-quinazoline-2-carboxylic acid |

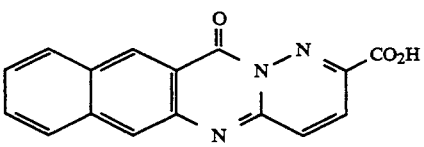

| | | 344–369 | 12-Oxo-12H-benzo[g]pyridazino[3,2-b]quinazoline-2-carboxylic acid |

The invention is further illustrated and the best mode is described in the following examples.

EXAMPLE 1

10-Oxo-10H-pyridazino[6,1-b]quinazoline-2,8-dicarboxylic acid

Step A. Ethyl 3-hydroxypyridazine-6-carboxylate [22.00 g, 0.13 mol, prepared from 3-hydroxypyridazine-6-carboxylic acid according to the procedure of Libermann, D. and Rouaix, A. (*Bull. Soc. Chim . Fr.* 1959, 1793–1798)] and phosphorous oxychloride (122 mL, 1.31 mol) were heated at 110° C. (via an oil bath) for 1 h. The mixture was cooled and concentrated under reduced pressure, which removed the excess phosphorous oxychloride. The residue was dissolved into chloroform, cooled, and carefully washed with saturated sodium bicarbonate solution. The chloroform extract was dried (MgSO$_4$) , filtered, concentrated and recrystallized from ethyl acetate-diisopropyl ether to afford ethyl 6-chloro-3-pyridazinecarboxylate as tan needles, mp 145°–150° C.

Step B. A mixture of 4-aminoisophthalic acid [prepared according to the procedure of Hirsh, J. A. and Schwartzkopf, G. (*J. Org. Chem.* 1974, 39, 2044–2048)]

ample 1, Step B) was heated as a melt at 165°–170° C. for 30 min. The oil was dissolved into chloroform, washed with 10% ammonium hydroxide solution, dried (MgSO$_4$) , filtered and concentrated. Medium pressure chromatography (silica gel, chloroform to 1% methanol in chloroform) of the crude oily-solid afforded 2-ethyl 8-methyl 10-oxo-10H-pyridazino[6,1-b]quinazoline-2,8-dicarboxylate as a yellow solid, mp 218°–221° C. dec.

Step D. A mixture of 2-ethyl 8-methyl 10-oxo-10H-pyridazino [6,1-b]quinazoline-2,8-dicarboxylate (0.15 g, 0.46 mmol, Example 1, Step C) in 50 mL of 10% hydrochloric acid was refluxed for 24 h. The mixture was cooled and filtered to give the titled compound as a yellow solid, mp>285° C.

EXAMPLE 2

8-[(4-Methylbenzoyl)amino]-10-oxo-10H-pyridazino [6,1-b]quinazoline-2-carboxylic acid Step A. To a stirring room temperature solution of ethyl 2-amino-5-nitrobenzoate (68. 1 g, 0.32 mol) and 4-dimethylaminopyridine (5.0 g, 0.04 mol) in 2 L of THF was added dropwise a solution of di-tert-butyl dicarbonate (74.2 g, 0.34 mol) in 50 mL of THF. The solution was stirred for 12 h, concentrated, redissolved into ethyl acetate and washed with saturated sodium bicarbonate and saturated sodium chloride solutions. The ethyl acetate extract was dried (MgSO$_4$), filtered, concentrated and recrystallized from diethyl ether-hexanes to give ethyl 2-[[(1,1-dimethylethoxy)carbonyl]amino]-5-nitrobenzoate as a tan solid, mp 118°–121° C.

Step B. A mixture of ethyl 2-[[1,1-dimethylethoxy)carbonyl]amino]-5-nitrobenzoate (50.10 g, 0.16 tool, Example 2, Step A) and 3 g of 5% palladium on carbon in 600 mL of THF: ethanol (1:1) was hydrogenated at room temperature at 52 psig hydrogen for 30 h. The mixture was filtered and concentrated. Chromatography (silica gel, chloroform to 2.5% methanol in chloroform) of the crude solid afforded ethyl 5-amino-2-[[1,1-dimethyl-ethoxy) carbonyl]amino]benzoate as a tan solid, mp 134°–138° C.

Step C. To a room temperature solution of ethyl 5-amino-2-[[1,1-dimethylethoxy) carbonyl]amino]benzoate (4.00 g, 14.27 mmol, Example 2, Step B) and triethylamine (2.2 mL, 15.78 mmol) in 250 mL of methylene chloride was added dropwise a solution of p-toluoyl chloride (2.0 mL, 15.12 mmol) in 50 mL of methylene chloride. The solution was stirred for 2 h, washed with saturated sodium bicarbonate solution, dried (MgSO$_4$), filtered and concentrated to give slightly crude ethyl 5-[(4-methylbenzoyl)amino]-2-[[1,1-dimethyl-ethoxy)carbonyl]amino]benzoate as a foamy dark yellow solid. The sample was dissolved into 250 mL of methylene chloride, treated with trifluoroacetic acid (10.0 mL, 130 mmol) and stirred at room temperature for 12 h. The solution was concentrated, redissolved into chloroform, washed with saturated sodium bicarbonate solution, dried (MgSO$_4$), filtered and concentrated. Recrystallization from ethyl acetate-diisopropyl ether gave ethyl 2-amino-5-[(4-methylbenzoyl)amino]benzoate as an off-white solid, mp 167°–171° C.

Step D. A mixture of ethyl 6-chloro-3-pyridazinecarboxylate (0.12 g, 0.64 mmol, Example 1, Step A) and ethyl 2-amino-5-[(4-methylbenzoyl)amino]benzoate (0.22 g, 0.74 mmol, Example 2, Step C) was heated as a melt at 165°–170° C. for 15 min. The resulting orange solid was suspended into saturated sodium bicarbonate solution, stirred at room temperature for 1 h then filtered. The solid was washed with water and diethyl ether to give ethyl 8-[(4-methyl-benzoyl)-amino]-10-oxo-10H-pyridazino[6,1-b]-quinazoline -2-carboxylate as an orange solid, mp 225°–230° C. dec.

Step E. A suspension of ethyl 8-[(4-methylbenzoyl)-amino]-10-oxo-10H-pyridazino[6,1-b]quinazoline -2-carboxylate (0.70 g, 1.74 mmol, Example 2, Step D) and 0.5M sodium carbonate solution (8.7 mL, 4.35 mmol) in 25 mL of THF:water (1:1) was gently refluxed for 2.5 h, during which time all the solid dissolved. Upon acidification with 10% hydrochloric acid, solid formed. The mixture was stirred at room temperature for 4 hr, filtered and washed with water and diethyl ether. The solid was recrystallized from pyridine to give the titled compound, pyridine salt as a yellow solid, mp 225°–257° C., dec.

In a process analogous to Example 2, using the appropriate starting materials, the corresponding compounds were prepared as follows:

EXAMPLE 2a 8- (Benzolyamino) -10-oxo-10H-pyridazino[6,1-b]quinazoline-2-carboxylic acid Orange solid, mp 265°–266° C., dec.

EXAMPLE 2b

8-[(4-Chlorobenzoyl)amino]-10-oxo-10H-pyridazino [6,1-b]quinazoline-2-carboxylic acid Orange solid, mp 253°–255° C., dec.

EXAMPLE 2c

8-[(4-Nitrobenzoyl)amino]-10-oxo-10H-pyridazino [6,1-b]quinazoline-2-carboxylic acid Orange solid, mp 250° C., dec.

EXAMPLE 2d

8-[(4-Iodobenzoyl)amino]-10-oxo-10H-pyridazino [6,1-b]quinazoline-2-carboxylic acid Orange solid, mp>325° C.

EXAMPLE 3

10-Oxo-10H-pyridazino[6,1-b]quinazoline-2,7-dicarboxylic acid

Step A. A mixture of ethyl 6-chloro-3-pyridazinecarboxylate (0.52 g, 2.79 mmol, Example 2, Step A) and dimethyl aminoterephthalate (0.61 g, 2.92 mmol, Aldrich Chemical Co.) was heated as a melt at 165°–170° C. for 15 min. The resulting brown solid was dissolved into 50 mL of chloroform:ethanol (4:1), washed with 50 mL of 10% ammonium hydroxide solution, dried (MgSO$_4$), filtered and concentrated. The crude oily solid was chromatographed (silica gel, 50% hexanes-50% ethyl acetate) to afford 2-ethyl 7-methyl 10-oxo-10H-pyridazino[6,1-b]quinazoline-2,7-dicarboxylate as a yellow solid, mp 202°–204° C. dec.

Step B. A suspension of 2-ethyl 7-methyl 10-oxo-10H-pyridazino[6,1-b]quinazoline-2,7-dicarboxylate (Example 3, Step A) in 10% hydrochloric acid was refluxed under nitrogen for 12 h. The mixture was cooled and filtered to give the titled compound as a yellow solid, mp>360° C.

EXAMPLE 4

7 -Acetylamino-10-oxo-10H-pyridazino[6,1-b]quinazoline-2-carboxylic acid

Step A. To a stirring solution at 0° C. under N$_2$ of ethyl 2,4-diaminobenzoate [5.00 g, 27.74 mmol, prepared according to the procedure of Keyser, G. E. and Leonard, N. J. (*J. Org. Chem.* 1976, 41, 3529–3532)] in 400 mL of methylene chloride was added dropwise a solution of acetic anhydride (2.6 mL, 27.56 mmol) in 100 mL of methylene chloride. The reaction was allowed to warm to room temperature overnight. The solution was concentrated, redissolved into ethyl acetate, cooled and carefully washed with saturated sodium bicarbonate solution. The ethyl acetate extract was dried (MgSO$_4$), filtered and concentrated. Medium pressure chromatography (silica gel, 2% methanol in chloroform) to afford ethyl 2-amino-4- (acetylamino) benzoate as a brown solid, mp 106°–109° C.

Step B. A solution of ethyl 2-amino-4-(acetylamino)-benzoate (4.03 g, 18.13 mmol, Example 4, Step A), p- toluenesulfonic acid, monohydrate (0.5 g, 2.63 mmol) and methyl 6-chloro-3-pyridazinecarboxylate [3.13 g, 18.14 mmol, prepared according to the procedure of Barlin, G. B. and Yap, C. Y. (Aust. J. Chem. 1977, 30, 2319–2322)] in 500 mL of toluene was refluxed under Dean-Stark conditions for 12 h. The mixture was concentrated, dissolved into chloroform, washed with saturated sodium bicarbonate solution, dried (MgSO₄), filtered and concentrated. Medium pressure chromatography (silica gel, 5% methanol in chloroform) afforded methyl 7-acetylamino-10-oxo-10H-pyridazino[6,1-b]-quinazoline-2-carboxylate as a yellow solid, mp 281°–285° C., dec.

Step C. A mixture of methyl 7-acetylamino-10-oxo-10H-pyridazino [6, 1-b]-quinazoline-2-carboxylate (0.38 g, 1.22 mmol, Example 4, Step B) and 0.5M sodium carbonate solution (6.0 mL, 3.0 mmol), Example 4, Step B) and 0.5M sodium carbonate solution (6.0 mL, 3.0 mmol) in 100 mL of THF:ethanol:water (1:1:2) was gently refluxed for 3 h. The resultant solution was filtered through a pad of Celite, concentrated, redissolved into water, acidified to a pH~ 1.5–2.0 with 10% hydrochloric acid and cooled. Solid formed, the mixture was filtered and washed with water, acetone and diethyl ether to give the titled compound as a dark yellow solid, mp 272°–275° C. dec Having described the invention, the embodiments of the invention in which an exclusive property or privilege is claimed are defined as follows:

1. A compound of the formula I

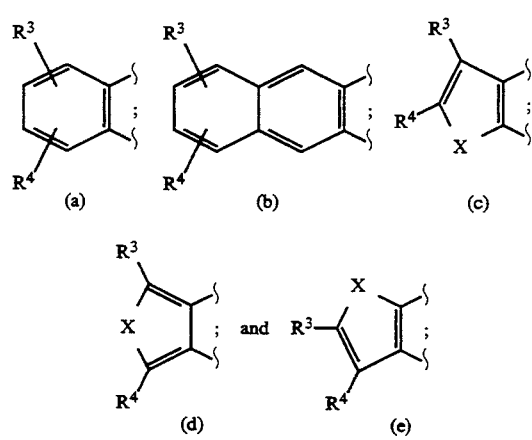

or a pharmaceutically acceptable salt thereof, wherein

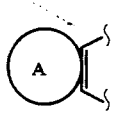

is a moiety selected from

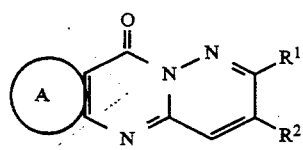

one of $R^1$ and $R^2$ is an acid group selected from —COOH, —SO₃H,

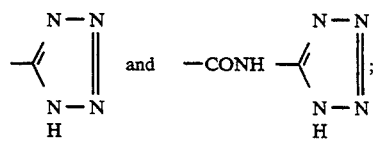

and the other of $R^1$ and $R^2$ is H or alkyl:

$R^3$ and $R^4$ can independently be H, —CONH₂, —CO—NH-aryl, —CO—NH-alkyl, —NHCO-alkyl, or —NHCO-aryl, in which alkyl is a straight or branched hydrocarbon moiety of 1–6 carbon atoms, and aryl is phenyl; and X is O, S or NH;

provided that, for a compound of formula I having moiety a) or b) wherein $R^1$ is COOH and $R^2$ is H, $R^3$ and $R^4$ represent a combination other than H and H.

2. A compound of claim 1 where:

$R^1$ is selected from the group consisting of —COOH,

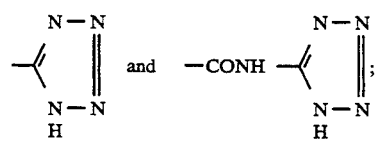

$R^2$ is H or methyl; and

is a moiety selected from

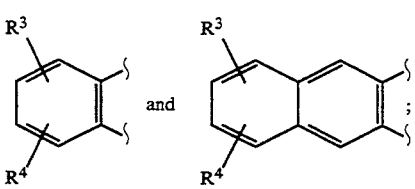

where one of $R^3$ and $R^4$ is H and the other is selected from —NHCO-aryl, and —NHCO-alkyl, in which alkyl is methyl and aryl is phenyl.

3. The compound having the name 8-[(4-methylbenzoyl)amino]-10-oxo-10H-pyridazino[6,1-b]quinazoline-2-carboxylic acid or a pharmaceutically acceptable salt thereof.

4. The compound having the name 8-(benzoylamino)-10-oxo-10H-pyridazino[6,1-b]quinazoline-2-carboxylic acid or a pharmaceutically acceptable salt thereof.

5. The compound having the name 8-[(4-chlorobenzoyl)amino]-10-oxo-10H-pyradazino[6,1-b]-quinazoline-2-carboxylic acid or a pharmaceutically acceptable slat thereof.

6. The compound having the name 8-[(4-nitrobenzoyl)amino]-10-oxo-10H-pyridazino[6,1-b]-quinazoline-2-carboxylic acid or a pharmaceutically acceptable salt thereof.

7. The compound having the name 8-[(4-iodobenzoyl)amino]-10-oxo-10H-pyridazino[6,1-b]-quinazoline- 2-carboxylic acid or a pharmaceutically acceptable salt thereof.

8. The compound having the name 7-acetylamino-10-oxo-10H-pyridazino[6,1-b]quinazoline-2-carboxylic acid or a pharmaceutically acceptable salt thereof.

9. A pharmaceutical composition useful for treating neurodegenerative disorders containing a therapeutically effective amount of a compound according to claim 1 in a pharmaceutically acceptable carrier.

10. A method for treating drug induced neuropathies in mammals which comprises administering to said mammal a pharmaceutical composition of claim 19.

11. A method for treating drug induced neuropathies in mammals comprising administering to said mammal in need of such treatment a therapeutically effective amount of 12-oxo-12H-benzo[g]pyridazino[3,2-b]quinazoline-2-carboxylic acid in a pharmaceutically acceptable carrier.

* * * * *

UNITED STATES PATENT AND TRADEMARK OFFICE
CERTIFICATE OF CORRECTION

PATENT NO. : 5,340,808  Page 1 of 2

DATED : August 23, 1994

INVENTOR(S) : Juan C. Jaen et al.

It is certified that error appears in the above-identified patent and that said Letters Patent is hereby corrected as shown below:

On column 2, line 5, please delete "et am.," and substitute therefore --et al.,--

On column 2, line 5, please delete "47:544-554," and substitute therefore --47:545-554,--

On column 4, lines 25 and 26, please delete "—CO-NH-arylalkyl, CO-NH-cycloalkyl, —CO-NH-alkylaryl," after the word "—CO-NH-alkyl"

On column 4, line 26, please insert ---—NHCO-aryl-- after the word "—NHCO-alkyl,"

On column 7, line 36, please delete "carboxylate" and substitute therefore -- -3-carboxylate--

On column 11, line 11, please delete "tool" and substitute therefore --mol--

On column 12, line 48, please delete "7" after the word "EXAMPLE 4"

On column 12, line 49, please insert --7-- before the word "-Acetylamino-"

On column 14, line 13 (claim 1), please delete ";and" after the word "phenyl"

UNITED STATES PATENT AND TRADEMARK OFFICE
CERTIFICATE OF CORRECTION

PATENT NO. : 5,340,808

DATED : August 23, 1994

INVENTOR(S) : Juan C. Jaen et al.

It is certified that error appears in the above-identified patent and that said Letters Patent is hereby corrected as shown below:

On column 14, line 62 (claim 5), please delete "slat" and substitute therefore --salt--

On column 14, line 50 (claim 2), please delete "." after the word "phenyl"

On column 14, line 50 (claim2), please insert --or phenyl substituted by methyl, chloro, iodo or nitro-- after the word "phenyl"

Signed and Sealed this

Third Day of January, 1995

Attest:

BRUCE LEHMAN

*Attesting Officer*  *Commissioner of Patents and Trademarks*